Jan. 24, 1950 E. S. BOERNER Plant Pat. 914
ROSE PLANT
Filed Dec. 2, 1948
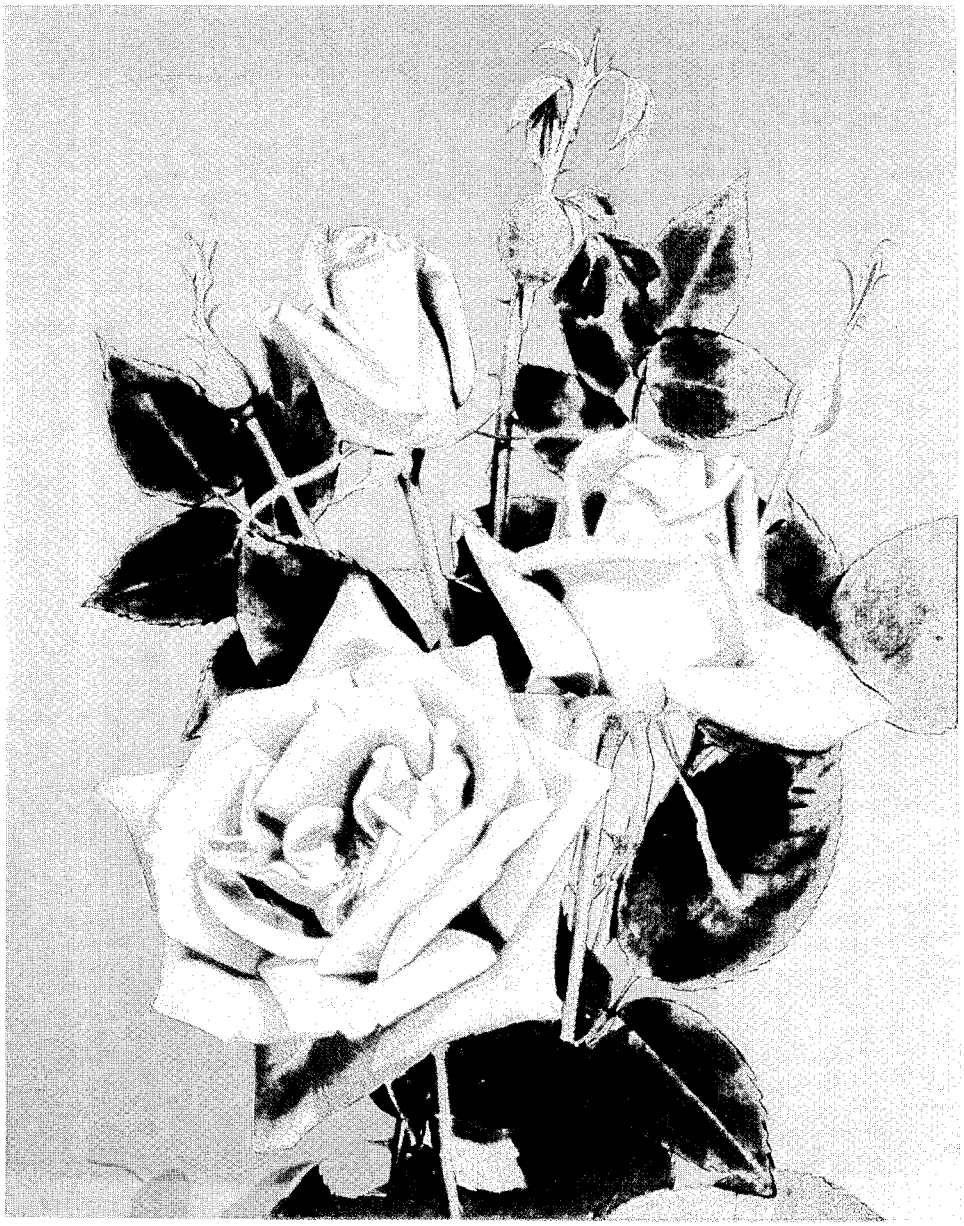
Inventor
E. S. Boerner
By Robb & Robb
Attorneys Patented Jan. 24, 1950

Plant Pat. 914

UNITED STATES PATENT OFFICE

914

ROSE PLANT

Eugene S. Boerner, Newark, N. Y., assignor to Jackson & Perkins Company, Newark, N. Y., a corporation of New York Application December 2, 1948, Serial No. 63,155

1 Claim. (Cl. 47—61)

This invention relates to a new and distinct variety of rose plant, distinguished from its parents and from other roses of its class by the uniformity of the coloring of its flowers which carries through from the bud to the open stage; by its long bud which opens to a high centered flower and by the unique characteristic marking of the two opposite petals of the outer row. This marking is of a yellow color showing through both sides of the petals and these two petals are streaked with Pomegranate Purple coloring.

In addition to the foregoing dominating characters, the young shoots bear a great number of thorns on the lower half of the stems, these thorns being close together in irregular formation and thinning out near the top of the shoots.

Asexual reproduction of this new variety shows the foregoing characteristics come true to form and are established.

In the accompanying drawing are shown specimens of the foliage and flowers at different stages of development and as true to color as possible.

The following is a detailed description of the new variety, color terminology being in accordance with Ridgway's Color Standards and Nomenclature:

Parentage: Seedling.

*Seed parent.*—"Poinsettia" (unpatented).

*Pollen parent.*—"Satan" (Pl. Pat. No. 379).

Classification: Botanic and commercial—hybrid tea.

*Flower*

Observations made at Newark, New York, in the month of October in the afternoon.

Blooming habit: Recurrent—continuous.

Bud:

*Size.*—Large.

*Form.*—Long. Is not affected by wet or hot weather.

*Color.*—When sepals first divide—Oxblood Red, Plate 1; when petals begin to unfurl—Tyrian Rose, Plate 12; when half blown—inside of petals—between Rose Red, Plate 12, and Tyrian Rose, Plate 12; reverse of petals—Tyrian Rose, Plate 12.

*Sepals.*—Branched, "hood" above bud. Curl back when petals begin to unfurl. Color—Inside—Chrysolite Green, Plate 31; outside—Light Bice Green, Plate 17.

*Calyx.*—Shape—funnel. Size—broad. Aspect—smooth. Odor when rubbed—none. Color—Yellowish Oil Green, Plate 5.

*Peduncle.*—Length—medium. Aspect—prickly. Color—Light Cress Green, Plate 31. Strength—erect; heavy.

*Opening.*—Opens up well. Is not affected by adverse conditions.

Bloom:

*Size.*—Very large. Average size when fully expanded, 5 inches.

*Borne.*—Singly and several together.

*Stems.*—Long; strong.

*Form.*—When first open—high center. Permanence—retains its form to the end.

*Petalage.*—Double (full but open center). Number of petals under normal conditions, 30.

*Color.*—Center of flower—Tyrian Rose, Plate 12. Outer petals—Tyrian Rose, Plate 12 (two opposite petals have a Marguerite Yellow, Plate 30, mark through the center, showing on both sides of the petal and extending almost to the tip. These petals also are streaked with Pomegranate Purple, Plate 12, coloring). Base of petals (aiglet)—Pale Viridine Yellow, Plate 5. Inside of petals—Tyrian Rose, Plate 12, overcast with Rose Red, Plate 12. Reverse of petals—Rose Color, Plate 12. General tonality from a distance—Tyrian Rose, Plate 12.

*Discoloration.*—General tonality at end of first day—Tyrian Rose, Plate 12. Second day—between Tyrian Rose, Plate 12, and Rose Color, Plate 12. Third day—Rose Color, Plate 12.

Petals:

*Texture.*—Thick; leathery. Is not affected by wet or hot weather.

*Appearance.*—Inside—satiny; outside—shiny.

*Form.*—Oval.

*Arrangement.*—Irregular. Petaloids in center—few; large.

*Persistence.*—Drop off cleanly.

*Fragrance.*—Moderate. Nature—tea (average hybrid tea scent).

*Lasting quality.*—On the plant and as cut flower—long.

Genital organs:

*Stamens, anthers.*—Medium size; many. Color—Mustard Yellow, Plate 16. Arrangement—Regular around styles.

*Stamens, filaments (threads).*—Medium length. Color—Pinard Yellow, Plate 4.

*Pollen.*—Color—Maize Yellow, Plate 4.

*Styles.*—Columnar, uneven length; medium length; heavy.
*Stigmas.*—Color—Baryta Yellow, Plate 4.
*Ovaries.*—All enclosed in calyx.

*Plant*

Form: Bush.
Growth: Vigorous, upright.
Foliage: 5 to 7 leaflets.
*Size.*—Large.
*Quantity.*—Abundant.
*Color.*—New foliage: upper side—Yellowish Oil Green, Plate 5, edges Oxblood Red, Plate 1; under side—Oxblood Red, Plate 1. Old foliage: upper side—Yew Green, Plate 31; under side—Light Cress Green, Plate 31.
*Shape.*—Oval pointed.
*Texture.*—Upper side—leathery; under side—rough. Ribs and veins—prominent.
*Edge.*—Serrated (saw toothed).
*Serration.*—Single; small.
*Leaf stem.*—Color—Deep Chrysolite Green, Plate 31. Under side—prickles.
*Stipules.*—Medium length; smooth.
*Disease resistance.*—Resistant.

Wood:
*New wood.*—Color—Orange Citrine, Plate 4. Bark—smooth.
*Old wood.*—Color—Cress Green, Plate 31. Bark—smooth.
Thorns:
*Thorns.*—On main stalks from base—many. On laterals from stalk—ordinary. Form—narrow base; medium length; hooked downward. Color when young—Neutral Red, Plate 38. Position—irregular.
*Prickles and short needles.*—None.

I claim:

A new and distinct variety of rose plant characterized as to novelty by the uniformity of the coloring of its flowers from bud to open stages; by the long buds opening into high centered flowers; by the distinct marking and streaking of the two opposite petals of the outer row of each flower, and the large number of thorns, closely arranged in irregular formation, on the lower half of the stems of the young shoots, substantially as shown and described.

EUGENE S. BOERNER.

No references cited.